US006192876B1

(12) United States Patent
Denyer et al.

(10) Patent No.: US 6,192,876 B1
(45) Date of Patent: Feb. 27, 2001

(54) INHALATION APPARATUS AND METHOD

(75) Inventors: Jonathan Stanley Harold Denyer, Chichester (GB); Kurt Nikander, Dalby (SE)

(73) Assignees: Astra Aktiebolag (SE); Medic-Aid Limited (GB)

( * ) Notice: Under 35 U.S.C. 154(b), the term of this patent shall be extended for 0 days.

(21) Appl. No.: 09/124,298

(22) Filed: Jul. 29, 1998

(30) Foreign Application Priority Data

Dec. 12, 1997 (SE) ............................................. 9704943-7

(51) Int. Cl.$^7$ ..................................................... A62B 18/08

(52) U.S. Cl. ................................ 125/205.25; 128/205.23; 128/204.18; 128/204.23; 128/206.15; 128/206.24

(58) Field of Search ......................... 128/205.25, 205.26, 128/205.27, 205.23, 200.24, 204.18, 204.21, 206.15, 206.16, 206.24, 204.23; 73/40

(56) References Cited

U.S. PATENT DOCUMENTS

| | | | | |
|---|---|---|---|---|
| 2,904,033 | * | 9/1959 | Shane | 128/205.23 |
| 3,580,051 | | 5/1971 | Blevins | 73/40 |
| 3,812,854 | | 5/1974 | Michaels et al. | 128/194 |
| 4,146,025 | * | 3/1979 | Warncke et al. | 128/205.23 |
| 4,533,082 | | 8/1985 | Maehara et al. | 239/102 |
| 4,765,325 | | 8/1988 | Crutchfield | 128/202.13 |
| 4,832,015 | | 5/1989 | Nowacki et al. | 128/205.23 |
| 4,846,166 | * | 7/1989 | Willeke et al. | 128/202.24 |
| 4,914,957 | * | 4/1990 | Dougherty | 73/40 |
| 5,148,802 | * | 9/1992 | Jaredeus et al. | 128/204.18 |
| 5,261,601 | | 11/1993 | Ross et al. | 239/102.2 |
| 5,265,595 | | 11/1993 | Rudolph | 128/204.18 |
| 5,517,983 | * | 5/1996 | Dieghan et al. | 128/204.23 |
| 5,535,739 | * | 7/1996 | Rapoport et al. | 128/204.23 |
| 5,577,497 | | 11/1996 | Mecikalski et al. | 128/203.15 |
| 5,601,078 | * | 2/1997 | Schaller et al. | 128/205.23 |
| 5,617,849 | * | 4/1997 | Springett et al. | 128/206.24 |
| 5,645,049 | | 7/1997 | Foley et al. | 128/203.29 |
| B1 5,148,802 | * | 8/1997 | Jardine et al. | 128/204.18 |

FOREIGN PATENT DOCUMENTS

| | | |
|---|---|---|
| 0 519 742 | 12/1992 | (EP) . |
| 0 627 266 | 12/1994 | (EP) . |
| 0 798 007 | 10/1997 | (EP) . |
| 1 568 808 | 6/1980 | (GB) . |
| 2 164 569 | 3/1986 | (GB) . |
| 93/12823 | 7/1993 | (WO) . |
| 94/07607 | 4/1994 | (WO) . |
| 96/01663 | 1/1996 | (WO) . |
| 96/09085 | 3/1996 | (WO) . |
| 96/13292 | 5/1996 | (WO) . |
| 96/13294 | 5/1996 | (WO) . |
| 97/07896 | 3/1997 | (WO) . |
| 97/09090 | 3/1997 | (WO) . |
| 97/11732 | 4/1997 | (WO) . |
| 97/29851 | 8/1997 | (WO) . |
| 97/48431 | 12/1997 | (WO) . |

OTHER PUBLICATIONS

Gebhart et al., J. Aerosol Sci., vol. 20, No. 2, pp. 141–147 (1989).

* cited by examiner

*Primary Examiner*—John G. Weiss
*Assistant Examiner*—V. Srivastava
(74) *Attorney, Agent, or Firm*—Fish & Richardson, P.C.

(57) ABSTRACT

An apparatus for and a method of ensuring the fit of a face mask to the face of a patient, the apparatus including a face mask having an inlet through which gas can be inhaled and a sensor for measuring the flow rate of gas drawn through the inlet of the face mask. The fit of the face mask is determined by monitoring the flow rate of gas drawn through the inlet of the face mask upon inhalation by a patient. The face mask is considered to satisfactorily fit the patient when a substantially regular inhalation waveform is achieved.

17 Claims, 7 Drawing Sheets

INHALATION APPARATUS AND METHOD

BACKGROUND OF THE INVENTION

The present invention relates to an apparatus for and a method of delivering a measured dose of medicament, typically a liquid or a powder in fluidised form, to a patient.

Nebulizers and inhalers have been developed for the delivery of medicament in a gas to a patient.

Inhalers broadly fall into two categories, these being pressurized metered dose inhalers (pMDI's) and dry powder inhalers (DPI's), which both have a mouthpiece through which a patient inhales. The effective use of inhalers can, however, prove difficult to a number of patients, notably paediatric patients.

With the traditional, or non breath-actuated, pressurized metered dose inhalers, this difficulty arises because effective operation of the inhaler requires a patient to actuate the inhaler at the onset of inhalation in order to draw the medicament deep into the lungs. Achieving this co-ordination is what is particularly difficult for paediatric patients. Typically, if the pressurized metered dose inhaler is actuated before the onset of inhalation most of the medicament will hit the back of the throat and if the pressurized metered dose inhaler is actuated after the onset of inhalation most of the medicament will remain in the throat or bronchial tracts where it will have no effect.

Breath-actuated pressurized metered dose inhalers and dry powder inhalers, whilst not requiring such co-ordination of actuation and inhalation, also prove difficult to use to paediatric patients because those inhalers require a patient to inhale with sufficient strength to achieve a particular flow rate, notably 30 l/min for dry powder inhalers, which in breath-actuated pressurized metered dose inhalers triggers the aerosol canister and in dry powder inhalers draws air through the inhaler. Paediatric patients in particular are not able to develop the necessary tidal volumes to achieve such flow rates. For paediatric patients, tidal volumes are typically in the range of from 10 to 150 ml giving rise to flow rates in the range of only from about 3 to about 15 l/min.

WO-A-96/01663 (in the name of Aradigm Corporation) and WO-A-97/07896 (in the name of Fluid Propulsion Technologies, Inc.) disclose examples of devices which have been developed to co-ordinate aerosol delivery with inhalation by a patient. Specifically, these devices are arranged to deliver an aerosol on sensing an inspiration flow rate above a specific minimum value.

To date, aerosols have been delivered to paediatric patients using a nebulizer or an inhaler in combination with a spacer. Whilst both of these systems provide a low velocity aerosol cloud which can be inhaled by a paediatric patient, usually over several breaths, the dose obtained by the patient can vary considerably and the patient has no indication as to the exact dose delivered.

This variability in dose stems essentially from the requirement for paediatric patients to use a face mask; paediatric patients being unable to grip a mouthpiece effectively. The use of a face mask, however, increases the dead space between the nebulizer or spacer and the patient. This is not usually a problem in adult patients as they generally have a tidal volume which far exceeds the dead space downstream of the nebulizer or spacer, and as such the dose received by the patient can be approximated with a fair degree of accuracy as the inhaled volume multiplied by the concentration of medicament in the gas.

WO-A-96/13294 (in the name of Medic-Aid et al) discloses an apparatus for and a method of delivering medicament to a patient for inhalation in which medicament is introduced into a chamber prior to inhalation and the total dose of medicament received by the patient is calculated based on the volume of the chamber, the amount of medicament introduced into the chamber, the time elapsed since the introduction of medicament into the chamber and the flow rate of gas drawn out of the chamber.

It is an aim of the present invention to provide an apparatus for and a method of delivering a measured dose of medicament more reliably and accurately to patients who develop only small tidal volumes and inhale only at low rates.

SUMMARY OF THE INVENTION

The present invention provides an apparatus for ensuring the fit of a face mask to the face of a patient, comprising:

a face mask having an inlet through which gas can be inhaled; and a sensor for measuring the flow rate of gas drawn through the inlet of the face mask;

wherein the fit of the face mask is determined by monitoring the flow rate of gas drawn through the inlet of the face mask upon inhalation by a patient, with the face mask being considered satisfactorily to fit the patient when a substantially regular inhalation waveform is achieved.

Preferably, the apparatus further comprises a chamber having an outlet in fluid communication with the inlet of the face mask. More preferably, the chamber includes an inlet through which gas can be introduced.

Preferably, the inlet of the face mask includes a one-way valve for preventing exhalation therethrough.

Preferably, the face mask has an outlet through which gas can be exhaled. More preferably, the outlet of the face mask includes a one-way valve for preventing inhalation therethrough.

Preferably, the apparatus further comprises display means for displaying information, such as the inhalation waveform, the peak amplitude of the inhalation waveform and the fit of the face mask to the face of the patient. More preferably, the display means comprises an LCD display or an LED display.

Preferably, the apparatus further comprises means for generating a sound when the face mask is fitted satisfactorily to the face of the patient.

The present invention also provides an apparatus for delivering medicament to a patient for inhalation, comprising:

a chamber for temporarily holding medicament prior to inhalation;

a device for introducing medicament into the chamber;

a face mask having an inlet through which gas can be inhaled; and fitting and calculation means for ensuring the fit of the face mask to the face of a patient and for calculating the total dose of medicament received by the patient, the fitting and calculation means including a sensor for measuring the flow rate of gas drawn out of the chamber and concentration determination means for determining the concentration of medicament in the chamber during each inhalation breath, the concentration of medicament decreasing with time owing at least in part to the deposition of medicament on internal surfaces of the chamber;

wherein the fit of the face mask is determined by monitoring the flow rate of gas drawn out of the chamber, and the total dose of medicament received by the patient is calculated by summing the dose of medicament received in each inhalation breath, the dose of medicament received in each inhalation breath being calculated as the amount of medicament inhaled from the chamber in the volume of that breath (e.g., by multiplying the concentration of medicament in the chamber during each inhalation by the volume of that breath) when compensated for by the volume of the dead space of the apparatus downstream of the chamber.

Preferably, the inlet of the face mask includes a one-way valve for preventing exhalation therethrough.

Preferably, the face mask has an outlet through which gas can be exhaled. More preferably the outlet of the face mask includes a one-way valve for preventing inhalation therethrough.

Preferably, the fitting and calculation means comprises a sensor for detecting the introduction of medicament into the chamber.

In one embodiment the sensor for measuring the flow rate of gas drawn out of the chamber and the sensor for detecting the introduction of medicament into the chamber are the same sensor.

In another embodiment the sensor for measuring the flow rate of gas drawn out of the chamber and the sensor for detecting the introduction of medicament into the chamber are separate sensors.

Preferably, the sensor for measuring the flow rate of gas drawn out of the chamber is located upstream of the device.

Preferably, the apparatus further comprises display means for displaying information, such as the inhalation waveform, the peak amplitude of the inhalation waveform, the fit of the face mask to the face of the patient, the concentration of medicament in the chamber, a warning when the concentration of medicament in the chamber falls below a predetermined threshold value and the dose of medicament received by the patient. More preferably, the display means comprises an LCD display or an LED display.

Preferably, the apparatus further comprises means for generating a sound when the face mask is fitted satisfactorily to the face of the patient, the concentration of medicament within the chamber falls below a predetermined threshold value and/or the required dose of medicament has been received by the patient.

In one embodiment the device comprises a nebulizer. Preferably, the nebulizer is one of a jet nebulizer, an ultrasonic nebulizer or a pressure mesh nebulizer.

In another embodiment the device comprises a pressurized aerosol container for delivering a metered dose of medicament.

In a further embodiment the device comprises a dry powder inhaler.

Preferably, the fitting and calculation means is adapted to actuate the device automatically when a satisfactory fit of the face mask to the face of the patient has been achieved.

Preferably, the fitting and calculation means includes a memory for storing data in a look-up table representing the decrease in concentration of medicament in the chamber over time, with the concentration determination means determining the concentration of medicament in the chamber during inhalation based on the data stored in the memory.

Preferably, the chamber includes an inlet for permitting the introduction of gas thereinto as gas is drawn out thereof by inhalation and thereby causes a decrease in the concentration of medicament in the chamber by dilution.

Preferably, the concentration determination means determines the concentration of medicament in the chamber based also on the volume of gas previously inhaled by the patient.

Preferably, the fitting and calculation means includes a memory for storing data in a look-up table representing the decrease in concentration of medicament in the chamber with the volume of gas previously inhaled.

Preferably, the chamber includes a first inlet through which gas is introduced thereinto and a second inlet which is in fluid communication with the device.

The present invention further provides an apparatus for delivering medicament to a patient for inhalation, comprising:

a nebulizer which in use generates an aerosol containing medicament for inhalation by a patient;

a face mask having an inlet through which gas can be inhaled; and fitting and calculation means for ensuring the fit of the face mask to the face of the patient and for calculating the total dose of medicament received by the patient, the fitting and calculation means including a sensor for measuring the flow rate of gas drawn through the face mask;

wherein the fit of the face mask is determined by monitoring the flow rate of gas drawn through the face mask, and the total dose of medicament received by the patient is calculated by summing the dose of medicament received in each inhalation breath, the dose of medicament received in each inhalation breath being calculated as the amount of medicament inhaled in the volume of that breath when compensated for by the volume of the dead space of the apparatus downstream of the nebulizer.

Preferably, the inlet of the face mask includes a one-way valve for preventing exhalation therethrough.

Preferably, the face mask has an outlet through which gas can be exhaled. More preferably, the outlet of the face mask includes a one-way valve for preventing inhalation therethrough.

Preferably, the apparatus further comprises display means for displaying information, such as the inhalation waveform, the peak amplitude of the inhalation waveform, the fit of the face mask to the face of the patient and the dose of medicament received by the patient. More preferably, the display means comprises an LCD display or an LED display.

Preferably, the apparatus further comprises means for generating a sound when the face mask is fitted satisfactorily to the face of the patient and/or the required dose has been received by the patient.

Preferably, the fitting and calculation means is adapted to actuate the nebulizer automatically when a satisfactory fit of the face mask to the face of the patient has been achieved.

In one embodiment the nebulizer includes a nebulizing space in which the aerosol is generated having an inlet through which gas can be inhaled and an outlet for connection to the face mask.

Preferably, the sensor is located upstream of the nebulizer.

Preferably, the nebulizer is one of a jet nebulizer, an ultrasonic nebulizer or a pressure mesh nebulizer.

The present invention still further provides a method of ensuring the fit of a face mask to the face of a patient, comprising the steps of:

fitting a face mask having an inlet through which gas can be inhaled to the face of a patient;

monitoring the flow rate of gas drawn through the inlet of the face mask as the patient inhales; and adjusting the position of the face mask as necessary until a substantially regular inhalation waveform is achieved.

In one embodiment a substantially regular inhalation waveform is achieved when the peak amplitude of the inhalation waveform is substantially at a maximum.

Preferably, the method further comprises the step of displaying information relating to the fit of the face mask, such as the inhalation waveform and the peak amplitude of the inhalation waveform.

Preferably, the method further comprises the step of providing an indication as to when the face mask is fitted satisfactorily to the face of the patient. In one embodiment the indication comprises displayed information. In another embodiment the indication comprises a sound.

The present invention yet further provides a method of delivering a dose of medicament to a patient for inhalation, using an apparatus comprising:

a chamber for temporarily holding medicament prior to inhalation;

a device for introducing medicament into the chamber;

a face mask having an inlet through which gas can be inhaled; and fitting and calculation means for ensuring the fit of the face mask to the face of a patient and for calculating the total dose of medicament received by the patient, the fitting and calculation means comprising a sensor for measuring the flow rate of gas drawn out of the chamber and concentration determination means for determining the concentration of medicament in the chamber during inhalation, the concentration of medicament decreasing with time owing at least in part to the deposition of medicament on internal surfaces of the chamber;

the method comprising the steps of:

providing fluid communication between the device and the face mask;

fitting the face mask to the face of a patient;

monitoring the flow rate of gas drawn out of the chamber as the patient inhales and adjusting the position of the face mask as necessary until a substantially regular inhalation waveform is achieved;

actuating the device to introduce medicament into the chamber; and calculating the total dose of medicament received by the patient by summing the dose of medicament received in each inhalation breath, the dose of medicament received in each inhalation breath being calculated as the amount of medicament inhaled from the chamber in by the volume of that breath when compensated for by the volume of the dead space of the apparatus downstream of the chamber.

In a first embodiment the method comprises the steps of providing fluid communication between the device and the face mask, fitting the face mask to the face of the patient and actuating the device in that named order.

In a second embodiment the method comprises the steps of providing fluid communication between the device and the face mask, actuating the device and fitting the face mask to the face of the patient in that named order.

In a third embodiment the method comprises the steps of fitting the face mask to the face of the patient, providing fluid communication between the device and the face mask and actuating the device in that named order.

In a fourth embodiment the method comprises the steps of fitting the face mask to the face of the patient, actuating the device and providing fluid communication between the device and the face mask in that named order.

In a fifth embodiment the method comprises the steps of actuating the device, providing fluid communication between the device and the face mask and fitting the face mask to the face of the patient in that named order.

In a sixth embodiment the method comprises the steps of actuating the device, fitting the face mask to the face of the patient and providing fluid communication between the device and the face mask in that named order.

In one embodiment a substantially regular inhalation waveform is achieved when the peak amplitude of the inhalation waveform is substantially at a maximum.

Preferably, the method further comprises the step of displaying information relating to the fit of the face mask, such as the inhalation waveform and the peak amplitude of the inhalation waveform.

Preferably, the method further comprises the step of providing an indication as to when the face mask is fitted satisfactorily to the face of the patient. In one embodiment the indication comprises displayed information. In another embodiment the indication comprises a sound.

Preferably, the method further comprises the step of displaying information relating to the dose of medicament received by the patient.

Preferably, the method further comprises the step of providing an indication as to when the required dose of medicament has been received by the patient. In one embodiment the indication comprises displayed information. In another embodiment the indication comprises a sound.

Preferably, the method further comprises the step of providing an indication as to when the concentration of medicament within the chamber falls below a predetermined threshold value. In one embodiment the indication comprises displayed information. In another embodiment the indication comprises a sound.

Preferably, the fitting and calculation means is adapted to actuate the device automatically when the a satisfactory fit of the face mask to the face of the patient has been achieved.

Preferably, the fitting and calculation means is adapted to actuate the device automatically when the concentration of medicament in the chamber falls below a predetermined threshold value.

The present invention still yet further provides a method of delivering a dose of medicament to a patient for inhalation, using an apparatus comprising:

a nebulizer which in use generates an aerosol containing medicament for inhalation by a patient;

a face mask having an inlet through which the patient can inhale; and fitting and calculation means for ensuring the fit of the face mask to the face of the patient and for calculating the total dose of medicament received by the patient, the fitting and calculation means including a sensor for measuring the flow rate of gas drawn through the face mask;

the method comprising the steps of:

providing fluid communication between the face mask and the nebulizer;

fitting the face mask to the face of a patient;

monitoring the flow rate of gas drawn through the face mask as the patient inhales and adjusting the position of the face mask as necessary until a substantially regular inhalation waveform is achieved;

actuating the nebulizer to generate an aerosol containing medicament; and calculating the total dose of medicament received by the patient by summing the dose of medicament received in each inhalation breath, the dose of medicament received in each inhalation breath being calculated as the amount of medicament inhaled in the volume of that breath when compensated for by the volume of the dead space of the apparatus downstream of the nebulizer.

In a first embodiment the method comprises the steps of providing fluid communication between the nebulizer and the face mask, fitting the face mask to the face of the patient and actuating the nebulizer in that named order.

In a second embodiment the method comprises the steps of providing fluid communication between the nebulizer and the face mask, actuating the nebulizer and fitting the face mask to the face of the patient in that named order.

In a third embodiment the method comprises the steps of fitting the face mask to the face of the patient, providing fluid communication between the nebulizer and the face mask and actuating the nebulizer in that named order.

In a fourth embodiment the method comprises the steps of fitting the face mask to the face of the patient, actuating the nebulizer and providing fluid communication between the nebulizer and the face mask in that named order.

In a fifth embodiment the method comprises the steps of actuating the nebulizer, providing fluid communication between the nebulizer and the face mask and fitting the face mask to the face of the patient in that named order.

In a sixth embodiment the method comprises the steps of actuating the nebulizer, fitting the face mask to the face of the patient and providing fluid communication between the nebulizer and the face mask in that named order.

In one embodiment a substantially regular inhalation waveform is achieved when the peak amplitude of the inhalation waveform is substantially at a maximum.

Preferably, the method further comprises the step of displaying information relating to the fit of the face mask, such as the inhalation waveform and the peak amplitude of the inhalation waveform.

Preferably, the method further comprises the step of providing an indication as to when the face mask is fitted satisfactorily to the face of the patient. In one embodiment the indication comprises displayed information. In another embodiment the indication comprises a sound.

Preferably, the method further comprises the step of displaying information relating to the dose of medicament received by the patient.

Preferably, the method further comprises the step of providing an indication as to when the required dose of medicament has been received by the patient. In one embodiment the indication comprises displayed information. In another embodiment the indication comprises a sound.

Preferably, the fitting and calculation means is adapted to actuate the nebulizer automatically when a satisfactory fit of the face mask has been achieved.

BRIEF DESCRIPTION OF THE DRAWINGS

Preferred embodiments of the present invention will now be described hereinbelow by way of example only with reference to the accompanying drawings, in which.

DETAILED DESCRIPTION OF THE PREFERRED EMBODIMENTS

Figure 1:
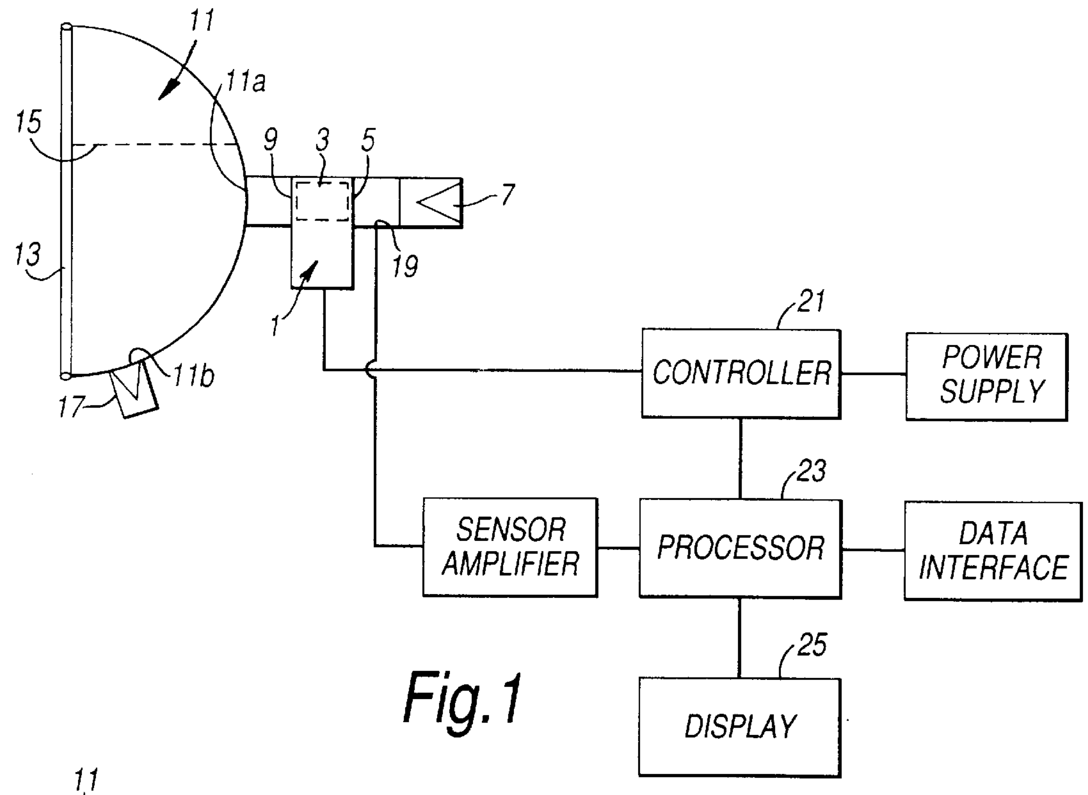
FIG. 1 illustrates an apparatus in accordance with a first embodiment of the present invention.

FIG. 1 illustrates an apparatus in accordance with a first embodiment of the present invention.

The apparatus includes a nebulizer 1 for generating an aerosol cloud containing medicament. The nebulizer 1 incorporates a nebulizing space 3 in which the aerosol cloud is generated, and has an inlet 5 to which is connected an inhalation valve 7 through which air can only be drawn from the atmosphere and an outlet 9 to which is connected a face mask 11.

In a preferred embodiment the nebulizer 1 comprises one of a jet nebulizer, an ultrasonic nebulizer or a pressure mesh nebulizer. Jet nebulizers are of two kinds, these being air jet nebulizers and liquid jet nebulizers. An example of an air jet nebulizer, which uses a source of compressed air to nebulize a liquid, is disclosed EP-A-0627266 (in the name of Medic-Aid Limited), the content of which is incorporated herein by reference. An example of a liquid jet nebulizer, which drives a liquid through one or more nozzle outlets to produce a spray of fine droplets, is disclosed in WO-A-94/07607 (in the name of Boehringer Ingelheim International GmbH et al), the content of which is incorporated herein by reference. Ultrasonic nebulizers, which nebulize a liquid using ultrasonic waves usually developed with an oscillating piezoelectric element, take many forms, these including nebulizers where liquid is in direct contact with the piezoelectric element, where there is an amplifying interface, typically an enclosed fluid, between the piezoelectric element and liquid, and where the piezoelectric element vibrates a mesh from which an aerosol is generated. Examples of ultrasonic nebulizers are disclosed in U.S. Pat. No. 4,533,082 (in the name of Maehara et al) and U.S. Pat. No. 5,261,601 (in the name of Ross et al), the contents of which are incorporated herein by reference. The nebulizers described in those documents include a housing that has a reservoir which holds a quantity of liquid to be dispensed, which housing has a perforated membrane in contact with the reservoir and an ultrasonic vibrator connected to the housing to vibrate the perforated membrane. Another example of an ultrasonic nebulizer is disclosed in WO-A-97/29851 (in the name of Fluid Propulsion Technologies, Inc.), the content of which is incorporated herein by reference. An example of a pressure mesh nebulizer, which may or may not include a piezoelectric element, is disclosed in WO-A-96/13292 (in the name of Aradigm Corporation), the content of which is incorporated herein by reference.

The face mask 11 includes an inlet 11*a* through which air can be inhaled and an outlet 11*b* through which air can be exhaled. The provision of the outlet 11*b* separate to the inlet 11*a* ensures that the dead space is restricted to within the face mask 11 and is preferable to having the outlet 11*b* at or upstream of the inlet 11*a* since in such a construction exhaled air may dilute aerosol resident upstream of the inlet 11*a* thereby increasing the reflective dead space. The face mask 11 further includes a flexible facial seal 13 which conforms in use to the contours of the face of a patient and provides the mask-to-patient seal. The facial seal 13 is a cushioned seal which can either be air or liquid filled. Face masks incorporating such facial seals are now common in the art and obviate the requirement for a head strap and the need to use high application forces which can be necessary with lip masks to ensure an adequate seal. One such facial seal is described in WO-A-97/09090 (in the name of Respironics, Inc.), the content of which is incorporated herein by reference. The face mask 11 also includes a nasal separator 15 for preventing fluid intercommunication between the nose and the mouth of a patient and ensuring a relatively small dead space within the face mask 11. One such face mask is disclosed in U.S. Pat. No. 5,265,595 (in the name of Hans Rudolph, Inc.), the content of which is incorporated herein by reference. The face mask 11 further includes an exhalation valve 17 at the outlet 11*b* through which air is exhaled and through which air cannot be inhaled.

The inhalation and exhalation valves 7, 17 of the nebulizer 1 and the face mask 11 are preferably of a low flow resistance design (typically 2.5 Pa @10 l/min) and ensure a perfect seal against reverse flow. Such valves are commercially available. One such valve is the valve incorporated in the NEBUCHAMBER (registered trade mark of Astra AB, Sweden) spacer.

The apparatus further includes a sensor 19 located upstream of the nebulizer 1 for measuring the flow rate of air drawn out of the nebulizing space 3, a controller 21 for controlling the operation of the nebulizer 1, a processor 23 for operating the controller 21 and for calculating the dose of medicament received by a patient, and a display 25 for displaying inter alia the flow rate of the air drawn out of the nebulizing space 3, the inhalation waveform and the dose of medicament received by a patient. The display 25 is preferably an LED or LCD display.

The apparatus further includes a data interface, such as a serial port, for providing communication with external devices.

In a preferred embodiment the apparatus includes means for informing the user, typically by the generation of a sound, when a satisfactory fit of the face mask 11 has been achieved and when the required dose of medicament has been delivered.

The sensor 19 is located in this embodiment at the inlet 5 to the nebulizer 1 and can be any of a pressure sensor, a microphone, a thermistor or an ultrasonic flow transducer which has the resolution necessary to measure the small volumes of air inhaled by paediatric patients. Typically, the resolution of the sensor 19 is required to be +/−0.25 l/min integrated at 10 ms intervals. In a preferred embodiment the sensor 19 is a pneumotach sensor. A pneumotach sensor is an air flow measurement device comprising a flow resistance element, typically a mesh which has a linear pressure-to-flow relationship, and a pressure sensor connected across the meshed duct, where the pressure measured is proportional to the flow in the duct.

Where the nebulizer 1 is an air jet nebulizer, the controller 21 will control the compressed air supply to the nebulizer 1, and where the nebulizer 1 is an ultrasonic nebulizer the controller 21 will control the electrical supply to the nebulizer 1. The controller 21 is preferably arranged to operate the nebulizer 1 to maintain an aerosol cloud of a predetermined concentration in the nebulizing space 3 throughout the breathing cycle, thereby optimizing delivery and ensuring that aerosol is available at the onset of inhalation without significant delay. In practice, an aerosol cloud can be developed which matches the minute volume of the patient by delivering aerosol intermittently or continuously but at a variable rate according to the inhalation flow rate. Such control is preferred to the alternative of triggering the nebulizer 1 only at the onset of inhalation, since if the nebulizer 1 were to be triggered only at the onset of inhalation then a delay of for example about 50 ms would be expected between triggering of the nebulizer 1 and the generation of aerosol, even using for example an efficient air jet nebulizer. This delay may decrease the efficiency of aerosol delivery, especially if the volume between the outlet 9 of the nebulizer 1 and the inlet 11*a* of the face mask 11 is non-minimal and contributes significantly to the dead space between the nebulizer 1 and a patient.

The processor 23 is connected both to the sensor 19 via an amplifier and the controller 21, and is arranged to send an operating signal to the controller 21 in response to the flow rate measured by the sensor 19 and the parameters set by a control program. In this embodiment, the processor 23 includes a clock, an analogue to digital converter for converting the analogue signal received from the sensor 19 into a digital signal, read only memory ROM containing the control program and look-up tables and random access memory RAM for storing measured data. The processor 23 is also connected to the display and to the data interface for providing communication with external devices. In a particularly preferred embodiment, the apparatus, including the processor 23, is battery powered.

In use, the user or the patient, who may be one and the same person, inputs into the processor 23 either the dose which is required or the medicament which is to be delivered for which there is a pre-set dose. The face mask 11 is then fitted to the patient, at which point the patient begins to breath therethrough. The patient draws air during inhalation through the nebulizing space 3 and exhales air through the exhalation valve 17 of the face mask 11. The flow rate developed by the patient is illustrated together with the inhalation waveform on the display 25. This illustrated waveform is monitored to determine when an effective seal is achieved between the face mask 11 and the face of the patient. An adequate seal is achieved when a substantially regular inhalation waveform is developed.

Figure 16:
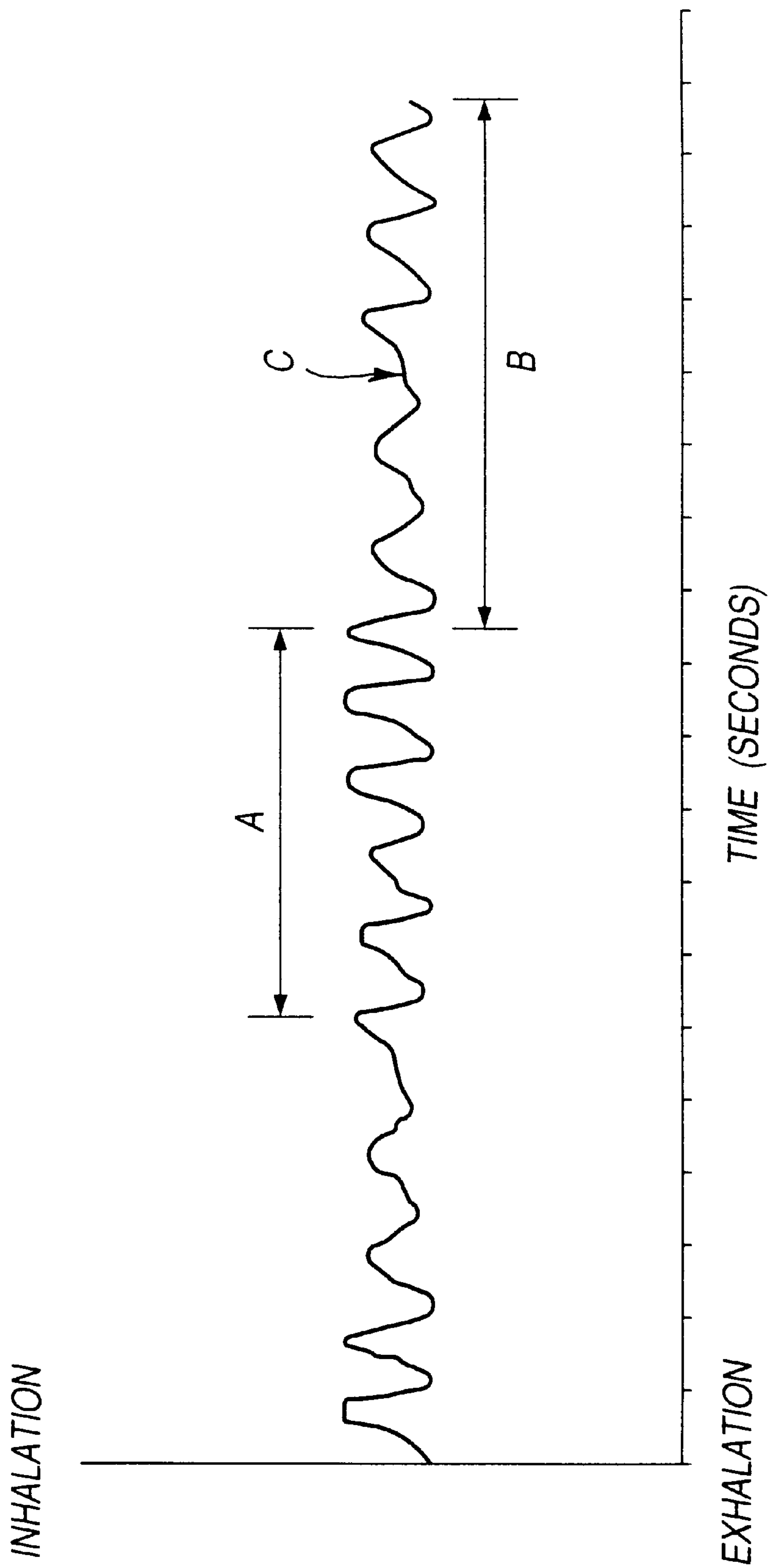
FIG. 16 illustrates a breathing pattern of a patient.

That is, when the peak amplitude of the inhalation waveform is maintained substantially at a maximum level as in region A of the breathing pattern illustrated in FIG. 16. In contrast, in region B of the breathing pattern illustrated in FIG. 16 the peak amplitude fluctuates indicating an imperfect sealing of the face mask 11 to the face of the patient. Indeed, region B of the breathing pattern includes a part (point C) where the patient has momentarily stopped breathing. In this regard, it will be noted that FIG. 16 illustrates the entire breathing pattern of a patient, whereas the sensor 19 which is located in a flow path that includes the inhalation valve 7 sees only the inhalation waveform of the breathing pattern. The achievement of a satisfactory fit of the face mask 11 will almost inevitably require some repositioning of the face mask 11. When an effective seal of the face mask 11 has been achieved, the nebulizer 1 is actuated to develop an aerosol cloud in the nebulizing space 3 at a predetermined concentration, and the patient continues to inhale. In a preferred embodiment a sound is generated and a message is displayed on the display 25 to inform the user that the face mask 11 is satisfactorily fitted to the face of the patient. In another preferred embodiment the nebulizer 1 is actuated automatically upon a satisfactory fit of the face mask 11 being achieved. As the patient inhales, aerosol containing medicament is drawn out of the nebulizing space 3 via the face mask 11 into his/her lungs. During inhalation the processor 23 continuously calculates the dose being delivered to the patient. In this embodiment, when the required dose has been delivered to the patient a message is displayed on the display 25 to this effect and a sound is generated, at which point the patient will then remove the face mask 11.

In practice, the processor 23 calculates the amount of medicament delivered to the patient at very frequent intervals, typically every one-hundredth of a second, during inhalation. This calculation is performed throughout each inhalation breath and is compensated so as to take into account the dead space of the apparatus downstream of the nebulizer 1.

For each inhalation breath (n=1, 2, 3 . . . ), the dose ($D_n$) received by the patient is calculated as:

$$D_n=(V_1+V_2+ \ldots +V_i)*C$$

where:

$V_1$ is the volume inhaled in the first sampled period in inhalation breath n after a volume corresponding to the dead space of the apparatus downstream of the nebulizing space 3 has been inhaled;

$V_2$ is the volume inhaled in the second sampled period in inhalation breath n after a volume corresponding to the dead space of the apparatus downstream of the nebulizing space 3 has been inhaled;

$V_i$ is the volume inhaled in the ith sampled period in inhalation breath n after a to volume corresponding to the dead space of the apparatus downstream of the nebulizing space 3 has been inhaled; and C is the concentration of medicament in the nebulizing space 3.

Thus, the total dose (D) of medicament delivered to a patient is the cumulative total of the dose delivered in each inhalation breath after a volume corresponding to the dead space of the apparatus downstream of the nebulizing space 3 has been inhaled, and can be expressed as follows:

$$D=D_1+D_2+ \ldots +D_n$$

where $D_n$ can represent an incomplete breath if the required dose is achieved during an inhalation breath.

As an approximation, where the inhalation waveform is a substantially cyclic waveform, the total dose of medicament delivered to a patient can be estimated as:

$$D=(V_t-V_d)*C*f*t$$

where:

$V_t$ is the tidal volume of each inhalation breath;

$V_d$ is the dead space of the apparatus downstream of the nebulizing space 3;

f is the frequency of inhalation; and t is the period of inhalation.

Figure 2:
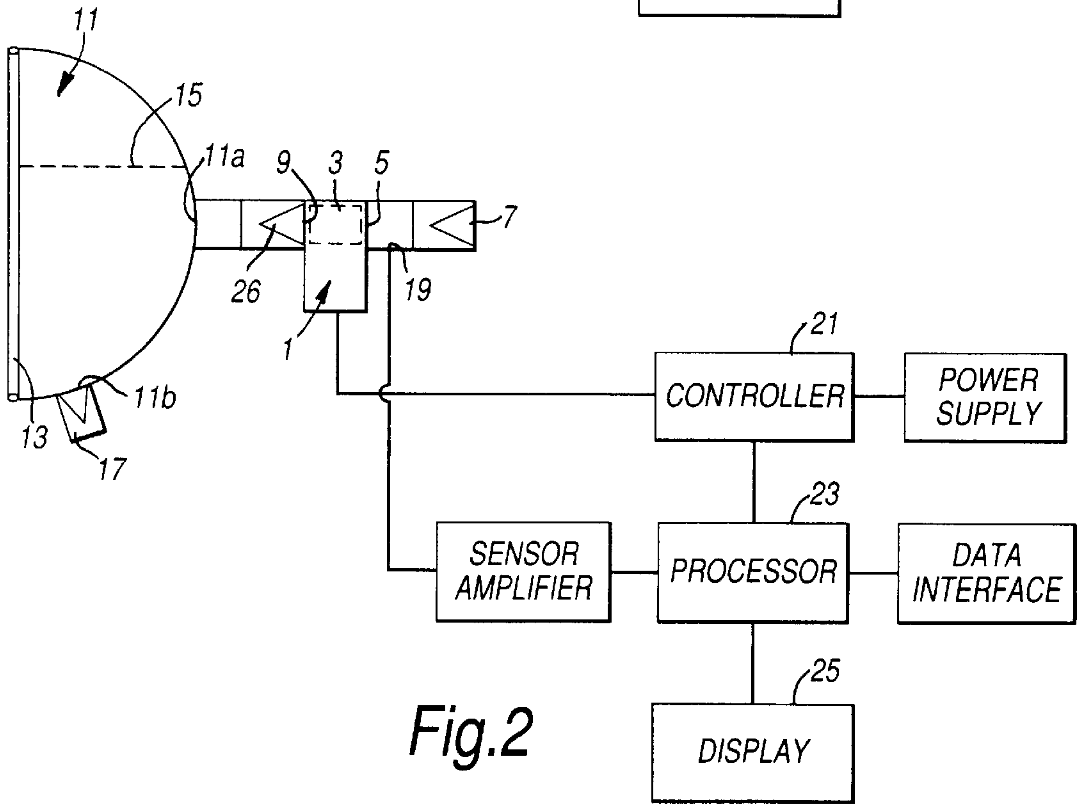
FIG. 2 illustrates an apparatus in accordance with a second embodiment of the present invention.

FIG. 2 illustrates an apparatus in accordance with a second embodiment of the present invention. This apparatus is of substantially the same construction as the apparatus of FIG. 1 except that the face mask 11 includes an inhalation valve 26 at the inlet 11*a* thereof for preventing exhalation therethrough. The inhalation valve 26 is, as with inhalation and exhalation valves 7, 17 of the nebulizer 1 and the face mask 11, preferably of a low flow resistance design. In a further alternative embodiment the inhalation valve 7 can be omitted. Operation of this apparatus is the same as for the apparatus of FIG. 1.

Figure 3:
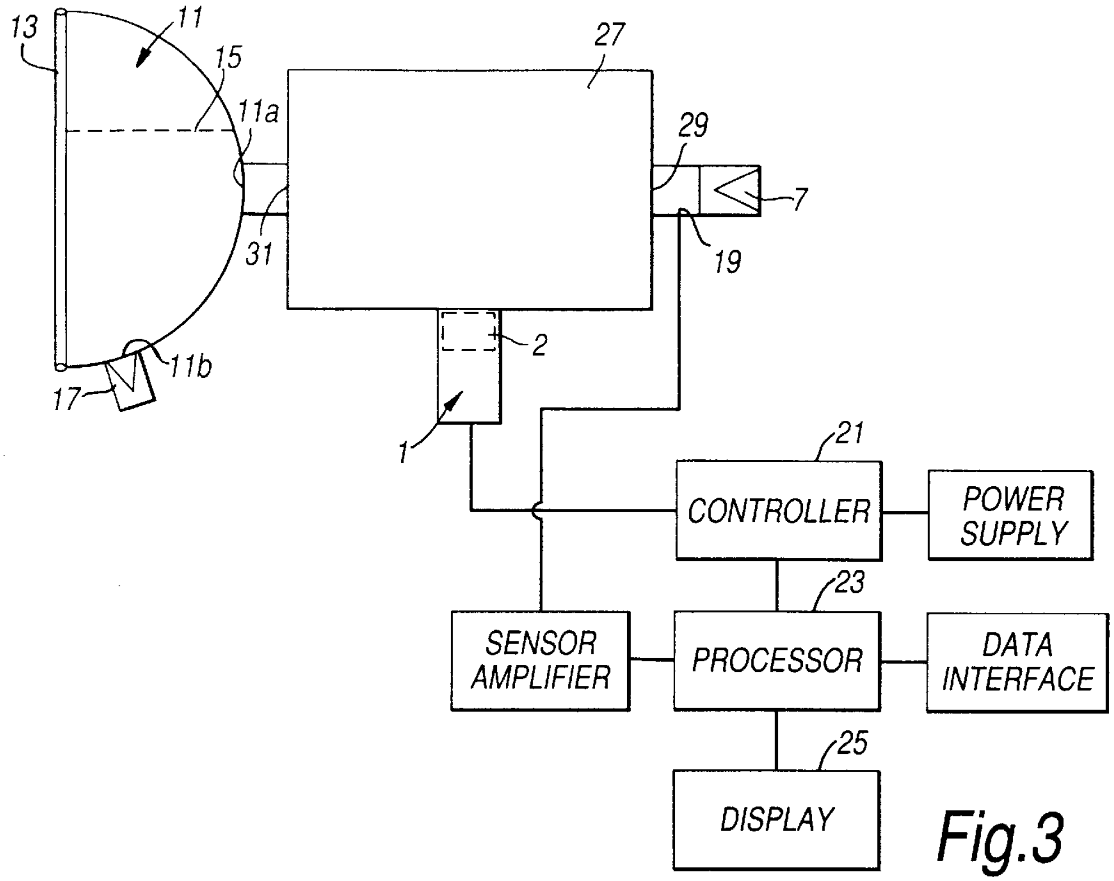
FIG. 3 illustrates an apparatus in accordance with a third embodiment of the present invention.

FIG. 3 illustrates an apparatus in accordance with a third embodiment of the present invention. This apparatus is of substantially the same construction as the apparatus of FIG. 1, but further includes a dispersion chamber 27, commonly referred to as a spacer, with which the nebulizing space 3 of the nebulizer 1 is in fluid communication. The chamber 27 includes an inlet 29 which is in fluid communication with the inhalation valve 7 and the sensor 19 and an outlet 31 which is in fluid communication with the inlet 11*a* of the face mask 11.

In a first mode, operation of this apparatus is the same as for the apparatus of FIG. 1, with the nebulizer 1 being controlled so as to maintain a predetermined concentration of medicament in the chamber 27.

In a second mode, operation of this apparatus is as follows. The user or the patient, which may be one and the same person, inputs into the processor 23 either the dose which is required or the medicament which is to be delivered for which there is a pre-set dose. The face mask 11 is then fitted to the patient, at which point the patient begins to inhale therethrough. The patient draws air during inhalation out of the chamber 27 and exhales air through the exhalation valve 17 of the face mask 11. The flow rate developed by the patient together with the inhalation waveform is illustrated on the display 25. This illustrated waveform is monitored to determine when an effective seal is achieved between the face mask 11 and the face of the patient. An adequate seal is achieved when a substantially regular inhalation waveform is developed as discussed hereinabove in relation to the use of the apparatus of FIG. 1. That is, when the peak amplitude of the inhalation waveform is maintained substantially at a maximum level. The achievement of a satisfactory fit of the face mask 11 will almost inevitably require some repositioning of the face mask 11. When a satisfactory fit of the face mask 11 has been achieved, the nebulizer 1 is then actuated and an aerosol containing medicament is provided in the chamber 27. In a preferred embodiment a sound is generated and a message is displayed on the display 25 to inform the user that the face mask 11 is satisfactorily fitted to the face of the patient. In another preferred embodiment the nebulizer 1 is actuated automatically upon a satisfactory fit of the face mask 11 being achieved. As the patient inhales, aerosol is withdrawn from the chamber 27 via the outlet 31 and the face mask 11 into his/her lungs. During inhalation the processor 23 continuously calculates the dose being delivered to the patient. In this embodiment, when the required dose has been delivered to the patient, a message is displayed on the display 25 to this effect and a sound is generated, at which point the patient will then remove the face mask 11.

The actual dose of medicament delivered to the patient is, however, dependent upon a number of factors as will be described hereinbelow and the calculation of the dose delivered to the patient is determined as a function of these factors.

With the elapse of time, the concentration of medicament in the chamber 27 decreases. This is both as a result of material settling on internal surfaces of the chamber 27 owing to gravitational and electrostatic forces, and as a result of the dilution effect caused by air from the atmosphere, which contains no medicament, being drawn into the chamber 27 with each inhalation breath by a patient to replace the inhalation volume.

Figure 4:
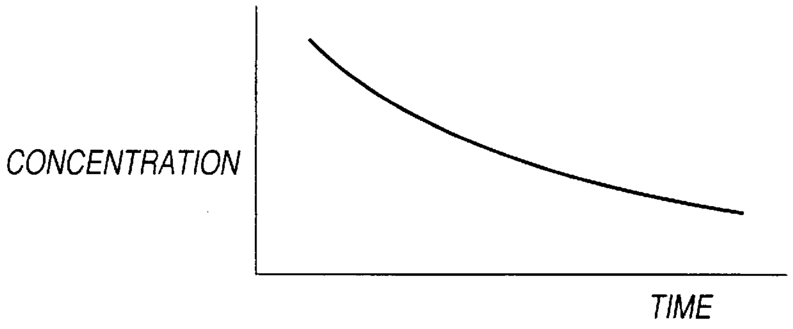
FIG. 4 illustrates graphically the variation in the concentration of medicament in the dispersion chamber of the apparatus of FIG. 3 with time.

The concentration of medicament in the chamber 27, and assuming no dilution, is dependent upon the time elapsed. The concentration of medicament in the chamber 27 as a function of time is illustrated in FIG. 4.

Figure 5:
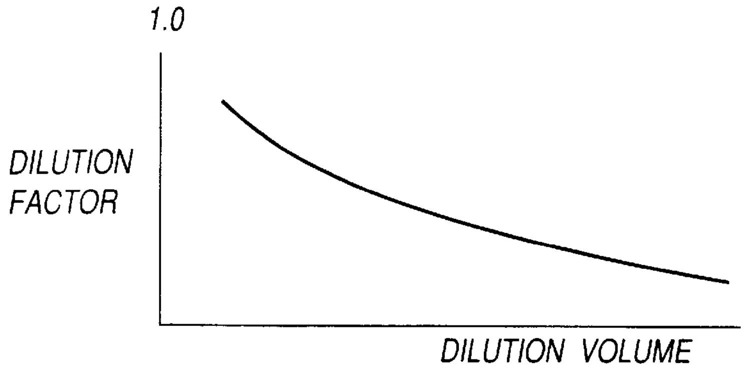
FIG. 5 illustrates graphically the dilution of medicament in the dispersion chamber of the apparatus of FIG. 3 with inhalation.

The dilution factor which is a function of the volume of air previously drawn by the patient out of the chamber 27 is illustrated in FIG. 5.

In practice, the processor 23 calculates the amount of medicament delivered to the patient at very frequent intervals, typically every one-hundredth of a second, during inhalation. In each of these sampled periods the concentration of medicament within the chamber 27 is calculated to take into account the deposition of medicament on internal surfaces of the chamber 27 with the elapse of time, and the dilution effect of air which does not carry any medicament entering the chamber 27. The read only memory ROM of the processor 23 contains a data look-up table which gives the concentration of medicament in the chamber 27 at any time after the introduction of medicament into the chamber 27 based upon the deposition rate of that medicament. The read only memory ROM also contains a data look-up table which gives the concentration of medicament in the chamber 27 following the introduction of a particular volume of air into the chamber 27. The concentration of medicament in the chamber 27 for each sampled period is thus calculated.

The dose of medicament delivered is then calculated. This calculation is performed continuously throughout each inhalation breath and is compensated so as to take into account the dead space of the apparatus downstream of the chamber 27.

For each inhalation breath (n=1, 2, 3 . . . ), the dose ($D_n$) received by the patient is calculated as:

$$D_n=V_1C_1+V_2C_2+ \ldots +V_iC_i$$

where:

$V_1$ is the volume inhaled in the first sampled period in inhalation breath n after a volume corresponding to the dead space of the apparatus downstream of the chamber 27 has been inhaled;

$V_2$ is the volume inhaled in the second sampled period in inhalation breath n after a volume corresponding to the dead space of the apparatus downstream of the chamber 27 has been inhaled;

$V_i$ is the volume inhaled in the ith sampled period in inhalation breath n after a volume corresponding to the dead space of the apparatus downstream of the chamber 27 has been inhaled;

$C_1$ is the calculated concentration in the first sampled period in inhalation breath n after a volume corresponding to the dead space of the apparatus downstream of the chamber 27 has been inhaled;

$C_2$ is the calculated concentration in the second sampled period in inhalation breath n after a volume corresponding to the dead space of the apparatus downstream of the chamber 27 has been inhaled; and $C_i$ is the calculated concentration in the ith sampled period in inhalation breath n after a volume corresponding to the dead space of the apparatus downstream of the chamber 27 has been inhaled.

Thus, the total dose (D) of medicament delivered to a patient is the cumulative total of the dose delivered in each inhalation breath after a volume corresponding to the dead space of the apparatus downstream of the chamber 27 has been inhaled, and can be expressed as follows:

$$D=D_1+D_2+ \ldots +D_n$$

where $D_n$ can represent an incomplete breath if the required dose is achieved during an inhalation breath.

Figure 6:
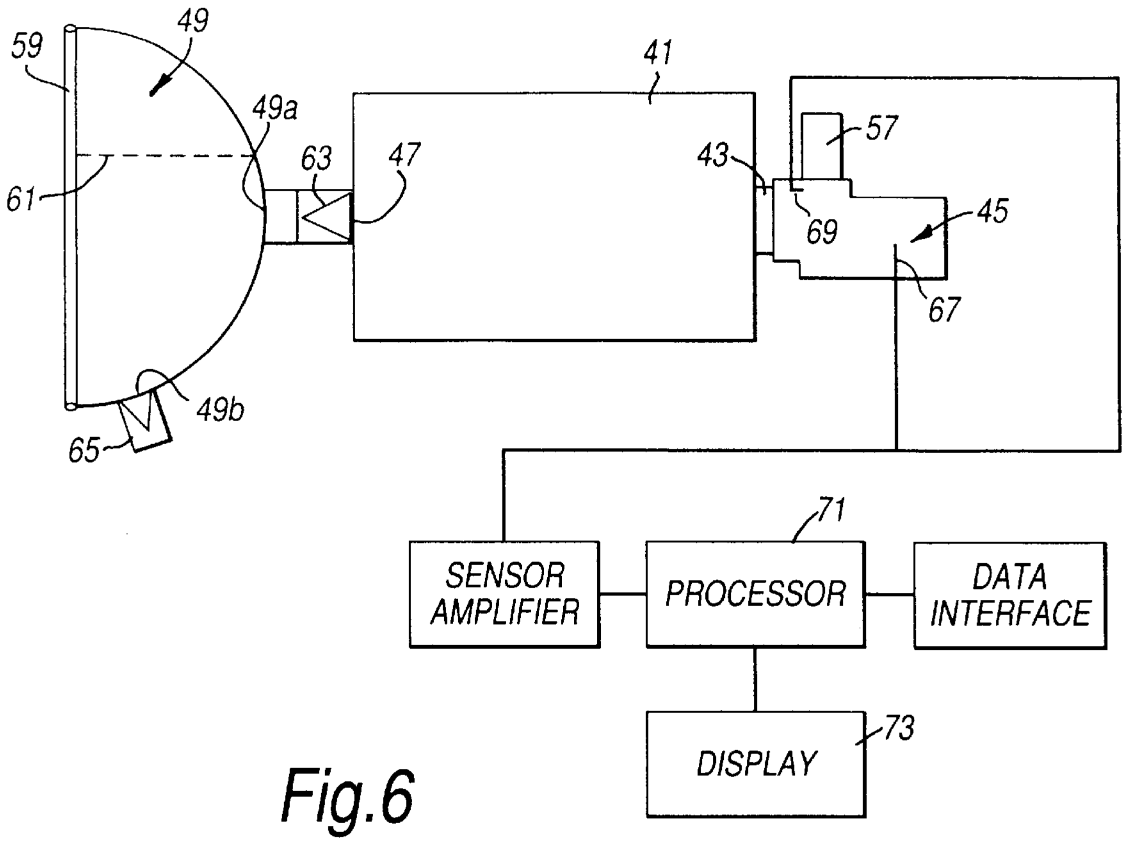
FIG. 6 illustrates an apparatus in accordance with a fourth embodiment of the present invention.
Figure 7:
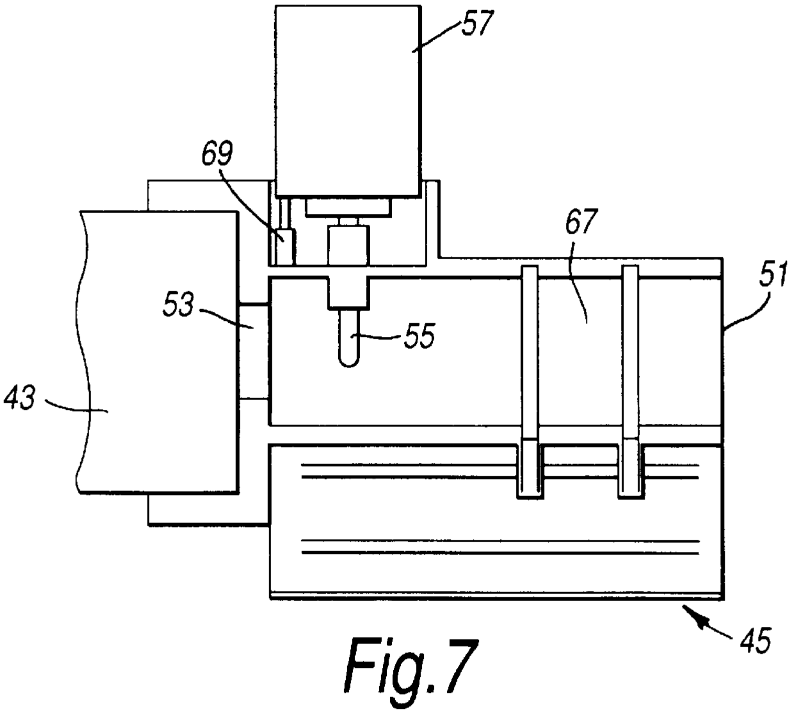
FIG. 7 illustrates in part cross-section the delivery unit of the apparatus of FIG. 6.

FIG. 6 illustrates an apparatus in accordance with a fourth embodiment of the present invention.

This apparatus includes a dispersion chamber 41, commonly referred to as a spacer, into which an aerosol cloud containing medicament is delivered. The chamber 41 has an inlet 43 to which is connected a delivery unit 45 and an outlet 47 to which is connected a face mask 49.

The delivery unit 45 has an inlet 51 through which air is in use inhaled and an outlet 53 which is in fluid communication with the inlet 43 of the chamber 41. The delivery unit 45 also includes a spray nozzle 55 which is adapted to receive the valve stem of a pressurised aerosol container 57 and direct an aerosol cloud containing medicament into the chamber 41. In this embodiment the container 57 on actuation delivers a metered dose of medicament.

The face mask 49 is of precisely the same kind as employed in the above-described second embodiment. Notably, the face mask 49 includes an inlet 49*a,* an outlet 49*b,* a flexible facial seal 59, a nasal separator 61, an inhalation valve 63 at the inlet 49*a* and an exhalation valve 65 at the outlet 49*b*.

The apparatus further includes a first sensor 67 for measuring the flow rate of air drawn out of the chamber 41 and a second sensor 69 for detecting each actuation of the container 57 in delivering medicament into the chamber 41. In this embodiment the first and second sensors 67, 69 form a part of the delivery unit 45. The first sensor 67 is located upstream of the spray nozzle 55 at the inlet 51 to the delivery unit 45 and can, as in the above-described embodiments, be any of a pressure sensor, a microphone, a thermistor or an ultrasonic flow transducer which has the resolution necessary to measure the small volumes of air inhaled by paediatric patients. In a preferred embodiment the first sensor 67 is a pneumotach sensor. In this embodiment the second sensor 69 is a micro-switch disposed so as to switched when the container 57 is actuated and a metered dose of medicament is delivered into the chamber 41. In an alternative embodiment the second sensor 69 can be omitted and the first sensor 67 used both to measure the flow rate of air drawn out of the chamber 41 and detect each actuation of the container 57. In another alternative embodiment the first sensor 67 can be located downstream of the spray nozzle 55.

The apparatus further includes a processor 71, which is connected to the first and second sensors 67, 69 via an amplifier, for calculating the dose of medicament received by a patient in accordance with the signals from the first and second sensors 67, 69 and a control program. In this embodiment the processor 71 includes a clock, an analogue to digital converter for converting the analogue signal received from the first sensor 67 into a digital signal, read only memory ROM containing the control program and look-up tables and random access memory RAM for storing measured data.

The apparatus also includes a display 73 which is connected to the processor 71 for displaying inter alia the flow rate of air drawn out of the chamber 41, the inhalation waveform and the dose of medicament delivered to a patient. The display 73 is again preferably an LED or LCD display.

The apparatus further includes a data interface, such as a serial port, which is connected to the processor 71 for providing communication with external devices.

As in the above-described embodiments, the apparatus preferably further includes means for informing the user, typically by the generation of a sound, when a satisfactory fit of the face mask 49 has been achieved and when the required dose of medicament has been delivered. The apparatus preferably also includes means for providing a warning if the concentration of medicament in the chamber 41 falls below a predetermined value which would necessitate a further actuation of the container 57. In a particularly preferred embodiment, the apparatus, including the processor 71, is battery powered.

In use, the user or the patient, which may be one and the same person, inputs into the processor 71 either the dose which is required or the medicament which is to be delivered for which there is a pre-set dose. The face mask 49 is then fitted to the patient, at which point the patient begins to inhale therethrough. The patient draws air during inhalation out of the chamber 41 and exhales air through the exhalation valve 65 of the face mask 49. The flow rate developed by the patient together with the inhalation waveform is illustrated on the display 73. This illustrated waveform is monitored to determine when an effective seal is achieved between the face mask 49 and the face of the patient. An adequate seal is achieved when a substantially regular inhalation waveform is developed as discussed hereinabove in relation to the use of the apparatus of FIG. 1. That is, when the peak amplitude of the inhalation waveform is maintained substantially at a maximum level. The achievement of a satisfactory fit of the face mask 49 will almost inevitably require some repositioning of the face mask 49. In a preferred embodiment a sound is generated and a message is displayed on the display 73 to inform the user that the face mask 49 is satisfactorily fitted to the face of the patient. When a satisfactory fit of the face mask 49 has been achieved, the container 57 is actuated at least once and an aerosol cloud containing medicament is released into the chamber 41. In accordance with usual practice where the medicament is a suspension in a propellant the container 57 is shaken prior to actuation so as to ensure a uniform suspension and thereby provide a precise dose of the medicament on actuation. As the patient inhales, medicament is withdrawn from the chamber 41 via the outlet 47 and the face mask 49 into his/her lungs. In a preferred embodiment a sound is generated and a message is displayed on the display 73 if the concentration of medicament in the chamber 41 falls below a predetermined value which would necessitate a further actuation of the container 57. During inhalation the processor 71 continuously calculates the dose being delivered to the patient. In this embodiment, when the required dose has been delivered to the patient a message is displayed on the display 73 to this effect and a sound is generated, at which point the patient will then remove the face mask 49.

The actual dose of medicament delivered to the patient is, however, dependent upon a number of factors as will be described hereinbelow and the calculation of the dose delivered to the patient is determined as a function of these factors.

With the elapse of time, the concentration of medicament in the chamber 41 decreases. This is both as a result of material settling on internal surfaces of the chamber 41 owing to gravitational and electrostatic forces, and as a result of the dilution effect caused by air from the atmosphere, which contains no medicament, being drawn into the chamber 41 with each inhalation breath by a patient to replace the inhalation volume.

Figure 8:
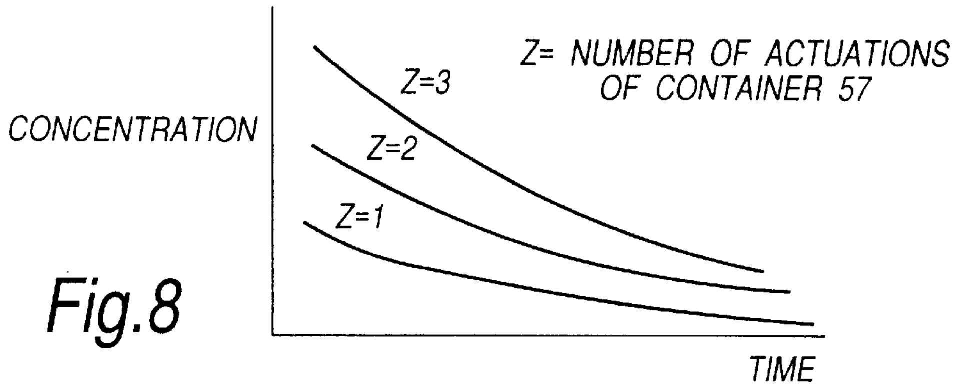
FIG. 8 illustrates graphically the variation in the concentration of medicament in the dispersion chamber of the apparatus of FIG. 6 with time.

The concentration of medicament in the chamber 41, and assuming no dilution, is dependent upon the time elapsed and the number of actuations of the container 57. The concentration of medicament in the chamber 41 as a function of time and the number of actuations of the container 57 is illustrated in FIG. 8.

Figure 9:
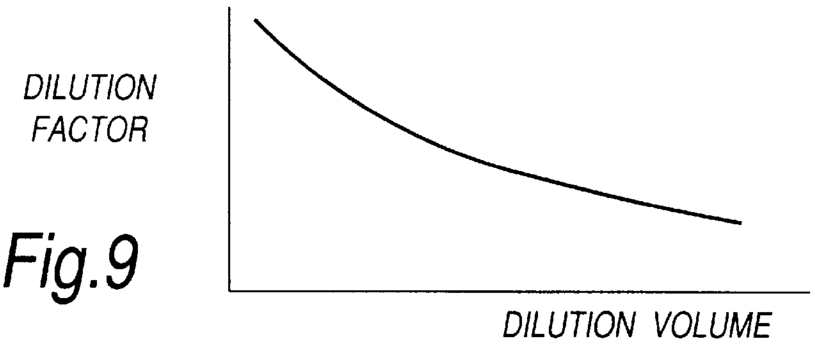
FIG. 9 illustrates graphically the dilution of medicament in the dispersion chamber of the apparatus of FIG. 6 with inhalation.

The dilution factor which is a function of the volume of air previously drawn by the patient out of the chamber 41 is illustrated in FIG. 9.

In practice, the processor 71 calculates the amount of medicament delivered to the patient at very frequent intervals, typically every one-hundredth of a second, during inhalation. In each of these sampled periods the concentration of medicament within the chamber 41 is calculated to take into account the deposition of medicament on internal surfaces of the chamber 41 with the elapse of time, and the dilution effect of air which does not carry any medicament entering the chamber 41. The read only memory ROM of the processor 71 contains a data look-up table which gives the concentration of medicament in the chamber 41 at any time after the introduction of medicament into the chamber 41 based upon the deposition rate of that medicament. The read only memory ROM also contains a data look-up table which gives the concentration of medicament in the chamber 41 following the introduction of a particular volume of air into the chamber 41. The concentration of medicament in the chamber 41 for each sampled period is thus calculated.

The dose of medicament delivered is then calculated. This calculation is performed continuously throughout each inhalation breath and is compensated so as to take into account the dead space of the apparatus downstream of the chamber 41.

For each inhalation breath (n=1, 2, 3 . . . ), the dose ($D_n$) received by the patient is calculated by integration as:

$$D_n=V_1C_1+V_2C_2+ \ldots +V_iC_i$$

where:

$V_1$ is the volume inhaled in the first sampled period in inhalation breath n after a volume corresponding to the dead space of the apparatus downstream of the chamber 41 has been inhaled;

$V_2$ is the volume inhaled in the second sampled period in inhalation breath n after a volume corresponding to the dead space of the apparatus downstream of the chamber 41 has been inhaled;

$V_i$ is the volume inhaled in the ith sampled period in inhalation breath n after a volume corresponding to the dead space of the apparatus downstream of the chamber 41 has been inhaled;

$C_1$ is the calculated concentration in the first sampled period in inhalation breath n after a volume corresponding to the dead space of the apparatus downstream of the chamber 41 has been inhaled;

$C_2$ is the calculated concentration in the second sampled period in inhalation breath n after a volume corresponding to the dead space of the apparatus downstream of the chamber 41 has been inhaled; and $C_i$ is the calculated concentration in the ith sampled period in inhalation breath n after a volume corresponding to the dead space of the apparatus downstream of the chamber 41 has been inhaled.

Thus, the total dose (D) of medicament delivered to a patient is the cumulative total of the dose delivered in each inhalation breath after a volume corresponding to the dead space of the apparatus downstream of the chamber 41 has been inhaled, and can be expressed as follows:

$$D=D_1+D_2+ \ldots +D_n$$

where $D_n$ can represent an incomplete breath if the required dose is achieved during an inhalation breath.

Figure 10:
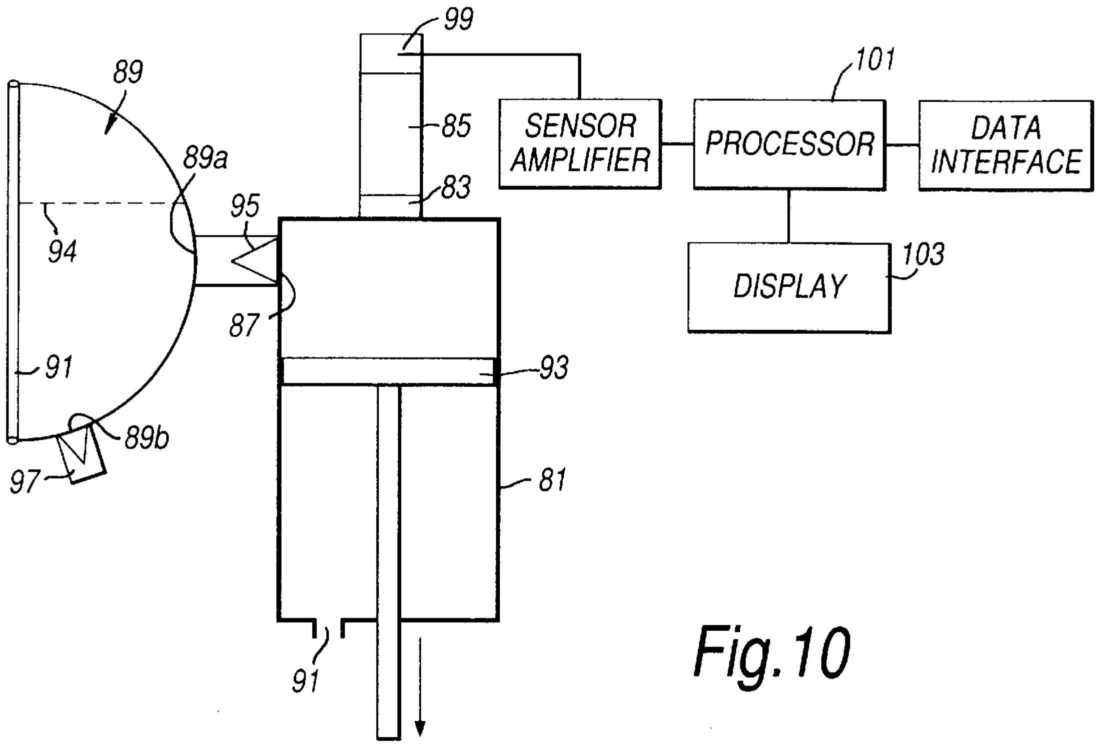
FIG. 10 illustrates an apparatus in accordance with a fifth embodiment of the present invention prior to actuation of the dry powder inhaler.
Figure 11:
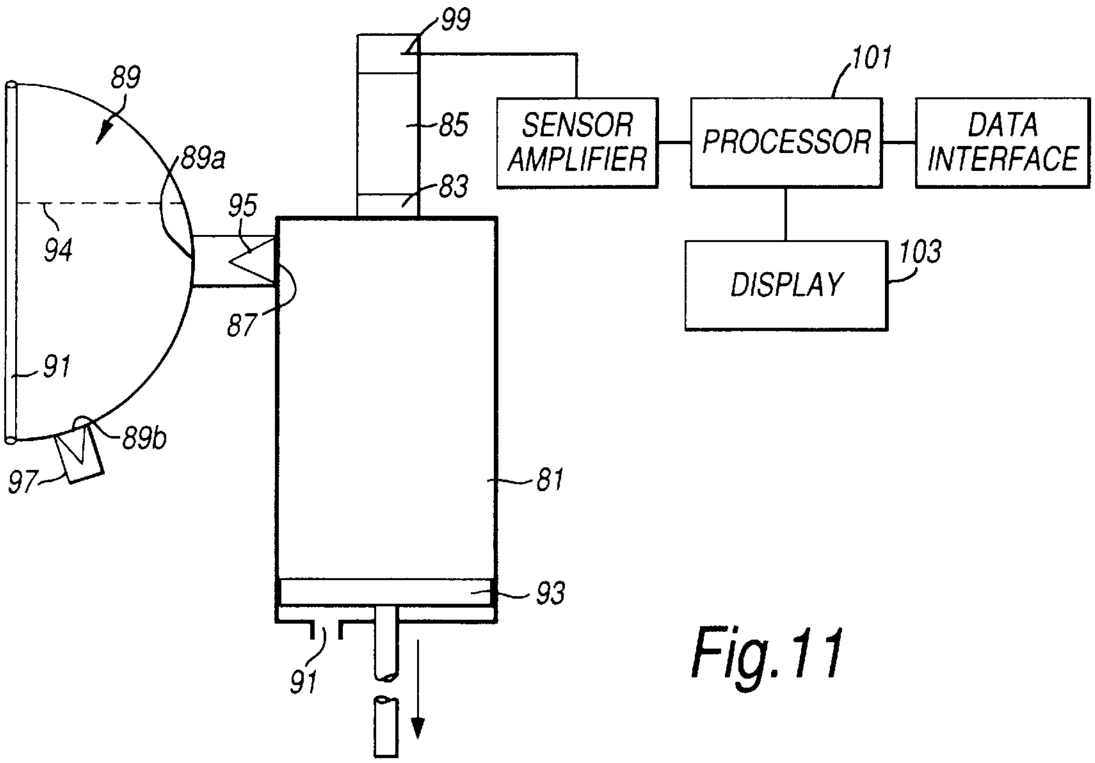
FIG. 11 illustrates the apparatus of FIG. 10 after actuation of the dry powder inhaler.

FIGS. 10 and 11 illustrate an apparatus in accordance with a fifth embodiment of the present invention. This apparatus is intended for use with a dry powder inhaler.

This apparatus includes a dispersion chamber 81, commonly referred to as a spacer, into which a dry powder containing medicament is dispersed. The chamber 81 has an inlet 83 to which is connected the outlet of a dry powder inhaler 85, which in use delivers a cloud of dry powder containing medicament into the chamber 81, an outlet 87 to which is connected a face mask 89, and a vent 91. The chamber 81 is of variable volume and is defined in part by a movable piston 92. In this embodiment, the dry powder inhaler 85 is a TURBUHALER (registered trade mark of Astra AB, Sweden) dry powder inhaler.

The face mask 89 is of precisely the same kind as employed in the above-described embodiment. That is, the face mask 89 includes an inlet 89*a,* an outlet 89*b,* a flexible facial seal 93, a nasal separator 94, an inhalation valve 95 at the inlet 89*a* and an exhalation valve 97 at the outlet 89*b.*

The apparatus further includes a sensor 99 located upstream of the inlet of the inhaler 85 for measuring the flow rate of air drawn out of the chamber 81 and detecting the actuation of the inhaler 85 in delivering medicament into the chamber 81, a processor 101 connected to the sensor 99 via an amplifier for calculating the dose of medicament received by a patient in accordance with signals received from the sensor 99 and a control program, and a display 103 for displaying inter alia the flow rate of air drawn out of the chamber 81, the inhalation waveform and the dose of medicament delivered to a patient. The display 103 is again preferably an LED or LCD display.

The apparatus also includes a data interface, such as a serial port, which is connected to the processor 101 for providing communication with external devices.

The sensor 99 can, as with the previously-described embodiments, be any of a pressure sensor, a microphone, a thermistor or an ultrasonic flow transducer which has the resolution necessary to measure the small volumes of air inhaled by paediatric patients. In a preferred embodiment the sensor 99 is a pneumotach sensor. In an alternative embodiment the sensor 99 can be located downstream of the inhaler 85.

In this embodiment the processor 101 includes a clock, an analogue to digital converter for converting the analogue signal received from the sensor 99 into a digital signal, read only memory ROM containing the control program and look-up tables and random access memory RAM for storing measured data.

In a preferred embodiment, as in the above-described embodiments, the apparatus further includes means for informing the user, typically by the generation of a sound, when a satisfactory fit of the face mask 89 has been achieved and when the required dose of medicament has been delivered. The apparatus preferably also includes means for providing a warning if the concentration of medicament in the chamber 81 falls below a predetermined value which would necessitate a further actuation of the inhaler 85. In a particularly preferred embodiment, the apparatus, including the processor 101, is battery powered.

In use, the user or the patient, which may be one and the same person, inputs into the processor 101 either the dose which is required or the medicament which is to be delivered for which there is a pre-set dose. The face mask 89 is then fitted to the patient, at which point the patient begins to breath therethrough. The patient draws air during inhalation through the inhaler 85 and out of the chamber 81 and exhales air through the exhalation valve 97 of the face mask 89. The flow rate developed by the patient together with the inhalation waveform is illustrated on the display 103. This illustrated waveform is monitored to determine when an effective seal is achieved between the face mask 89 and the face of the patient. An adequate seal is achieved when a substantially regular inhalation waveform is developed as discussed hereinabove in relation to the use of the apparatus of FIG. 1. That is, when the peak amplitude of the inhalation waveform is maintained substantially at a maximum level. The achievement of a satisfactory fit of the face mask 89 will almost inevitably require some repositioning of the face mask 89. In a preferred embodiment a sound is generated and a message is displayed on the display 103 to inform the user that the face mask 89 is satisfactorily fitted to the face of the patient. When a satisfactory fit of the face mask 89 has been achieved, the inhaler 85 is then primed and actuated. The inhaler 85 is actuated by moving the piston 92 to the position illustrated in FIG. 10 and then releasing the same. In this embodiment, the piston 92 is spring-mounted such that on release the piston 92 is driven, downwardly in FIG. 10, to the position of FIG. 11, so as to develop the required flow profile at the outlet of the inhaler 85 and thereby ensure the optimum dispersion of powder in the chamber 81. As the patient inhales, powder containing medicament is drawn out the chamber 81 via the outlet 87 and the face mask 89 into his/her lungs. In a preferred embodiment a sound is generated and a message is displayed on the display 103 if the concentration of medicament in the chamber 81 falls below a predetermined value which would necessitate a further actuation of the inhaler 85. During inhalation the processor 101 continuously calculates the dose being delivered to the patient. In this embodiment, when the required dose has been delivered to the patient a message is displayed on the display 103 to this effect and a sound is generated, at which point the patient will then remove the face mask 89.

The actual dose of medicament delivered to the patient is, however, again dependent upon a number of factors and the calculation of the dose delivered to the patient is determined as a function of these factors.

With the elapse of time, the concentration of medicament in the chamber 81 decreases. This is both as a result of material settling on internal surfaces of the chamber 81 owing to gravitational and electrostatic forces, and as a result of the dilution effect caused by air from the atmosphere, which contains no medicament, being drawn into the chamber 81 with each inhalation breath by a patient to replace the inhalation volume.

Figure 12:
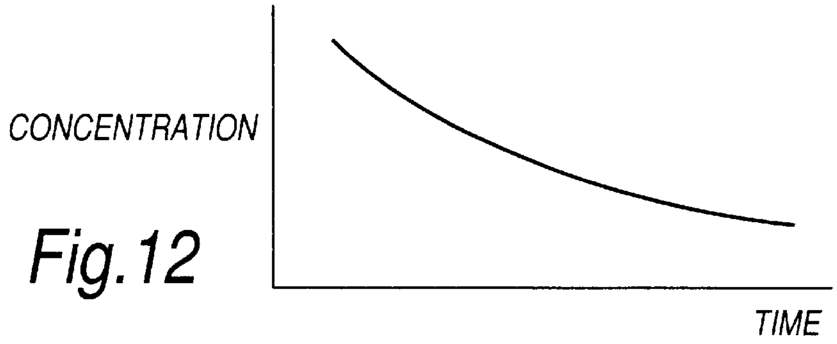
FIG. 12 illustrates graphically the variation in the concentration of medicament in the dispersion chamber of the apparatus of FIG. 10 with time.

The concentration of medicament in the chamber 81, and assuming no dilution, is dependent upon the time elapsed. The concentration of medicament in the chamber 81 as a function of time is illustrated in FIG. 12.

Figure 13:
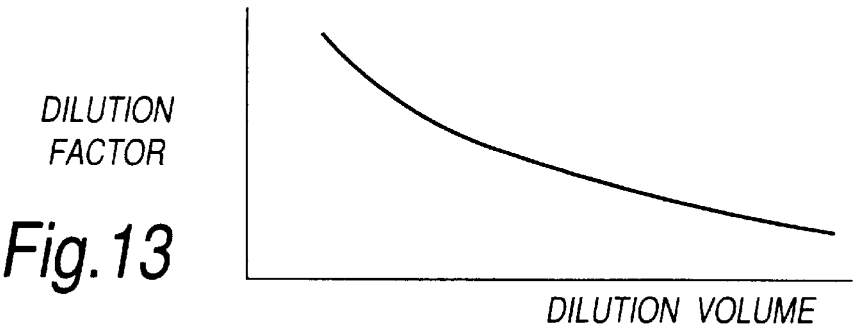
FIG. 13 illustrates graphically the dilution of medicament in the dispersion chamber of the apparatus of FIG. 10 with inhalation.

The dilution factor which is a function of the volume of air drawn by the patient out of the chamber 81 is illustrated in FIG. 13.

In practice, the processor 101 calculates the amount of medicament delivered to the patient at very frequent intervals, typically every one-hundredth of a second, during inhalation. In each of these sampled periods the concentration of medicament within the chamber 81 is calculated to take into account the deposition of medicament on internal surfaces of the chamber 81 with the elapse of time, and the dilution effect of air which does not carry any medicament entering the chamber 81. The read only memory ROM of the processor 101 contains a data look-up table which gives the concentration of medicament in the chamber 81 at any time after the introduction of medicament into the chamber 81 based upon the deposition rate of that medicament. The read only memory ROM also contains a data look-up table which gives the concentration of medicament in the chamber 81 following the introduction of a particular volume of air into the chamber 81. The concentration of medicament in the chamber 81 for each sampled period is thus calculated, from which the dose of medicament delivered to the patient is then calculated. This calculation is performed continuously throughout each inhalation breath and is compensated so as to take into account the dead space of the apparatus downstream of the chamber 81.

For each inhalation breath (n=1, 2, 3 . . . ), the dose ($D_n$) received by the patient is calculated by integration as:

$$D_n=V_1C_1+V_2C_2+ . . . +V_iC_i$$

where:

$V_1$ is the volume inhaled in the first sampled period in inhalation breath n after a volume corresponding to the dead space of the apparatus downstream of the chamber 81 has been inhaled;

$V_2$ is the volume inhaled in the second sampled period in inhalation breath n after a volume corresponding to the dead space of the apparatus downstream of the chamber 81 has been inhaled;

$V_i$ is the volume inhaled in the ith sampled period in inhalation breath n after a volume corresponding to the dead space of the apparatus downstream of the chamber 81 has been inhaled;

$C_1$ is the calculated concentration in the first sampled period in inhalation breath n after a volume corresponding to the dead space of the apparatus downstream of the chamber 81 has been inhaled;

$C_2$ is the calculated concentration in the second sampled period in inhalation breath n after a volume corresponding to the dead space of the apparatus downstream of the chamber 81 has been inhaled; and $C_i$ is the calculated concentration in the ith sampled period in inhalation breath n after a volume corresponding to the dead space of the apparatus downstream of the chamber 81 has been inhaled.

Thus, the total dose (D) of medicament delivered to a patient is the cumulative total of the dose delivered in each inhalation breath after a volume corresponding to the dead space of the apparatus downstream of the chamber 81 has been inhaled, and can be expressed as follows:

$$D=D_1+D_2+ . . . +D_n$$

where $D_n$ can represent an incomplete breath if the required dose is achieved during an inhalation breath.

Figure 14:
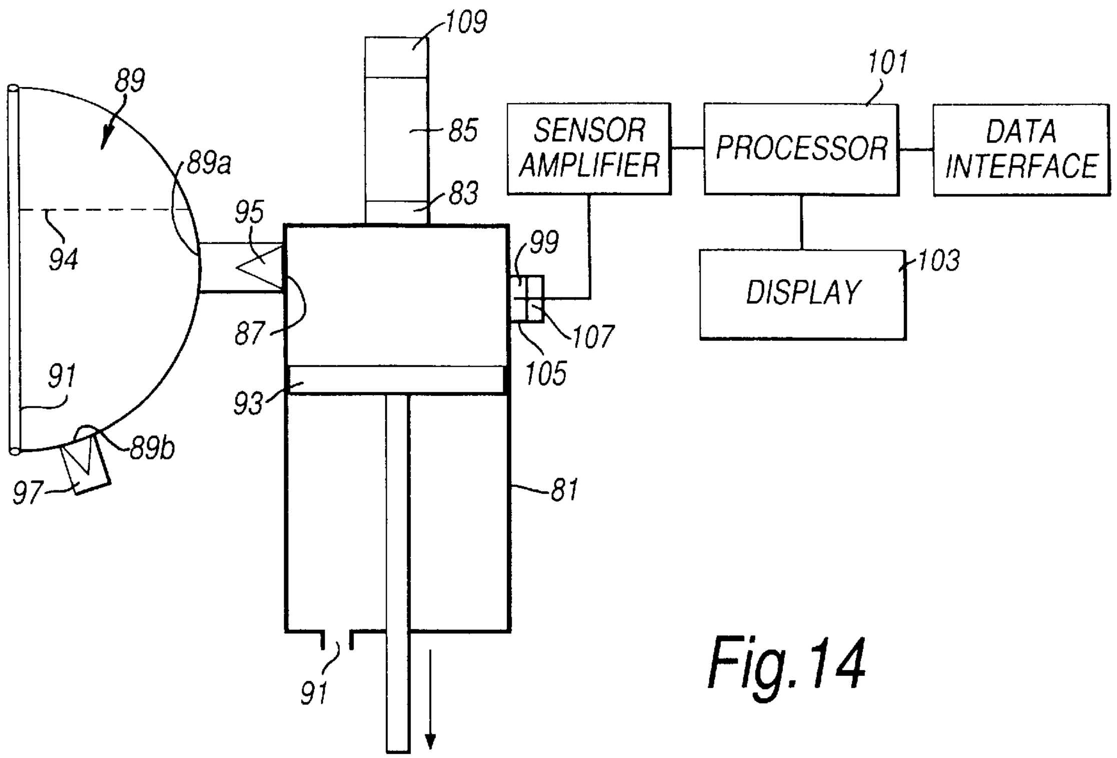
FIG. 14 illustrates an apparatus in accordance with a sixth embodiment of the present invention prior to actuation of the dry powder inhaler.
Figure 15:
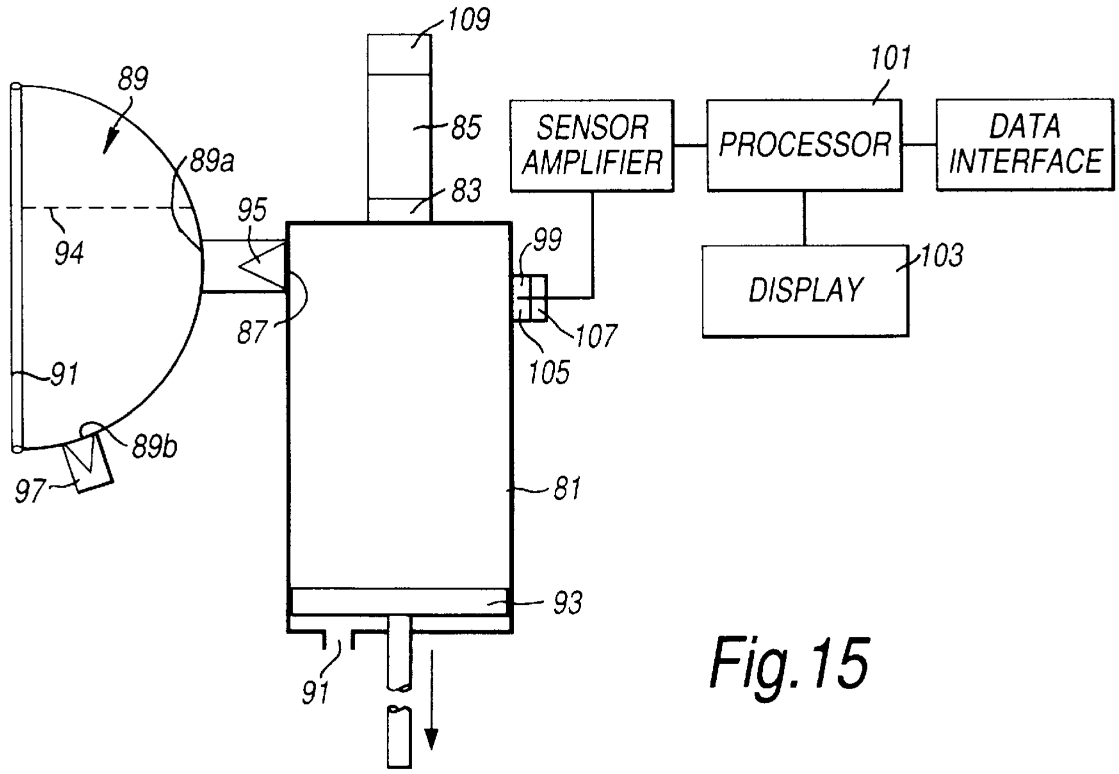
FIG. 15 illustrates the apparatus of FIG. 14 after actuation of the dry powder inhaler.

FIGS. 14 and 15 illustrate an apparatus in accordance with a sixth embodiment of the present invention. This apparatus is of substantially the same construction as the apparatus of FIGS. 10 and 11 and differs essentially in that the sensor 99 is provided in a further inlet 105 to the chamber 81. The apparatus also includes a valve 107 at the further inlet 105 which is normally open so as to allow inhalation therethrough except at the instant when the inhaler 85 is actuated. The apparatus further includes a valve 109 at the inlet 83 to the inhaler 85 which is normally closed except at the instant when the inhaler 85 is actuated, the valve 109 being open at that instant so as to allow air to be drawn through the inhaler 85 and entrain dry powder containing medicament from within the inhaler 85. In this embodiment the valves 107, 109 are electrically operated in response to actuation of the inhaler 85. Operation of this apparatus is the same as for the apparatus of FIGS. 10 and 11.

Finally, it will be understood that the present invention is not restricted to the described embodiments but can be modified in many different ways without departing from the scope of the appended claims.

What is claimed is:

1. An apparatus for ensuring the fit of a face mask to the face of a patient, comprising:

a face mask which includes an inlet through which gas can be inhaled;

a sensor for measuring the flow rate of gas drawn through the inlet of the face mask and providing a signal indicating said flow rate, said signal having breath cycle waveforms;

a processor that receives and analyzes said signal and compares flow rate waveforms to determine if they are substantially uniform over a plurality of breath cycles, and an indicator for providing an indication as to when the face mask is satisfactorily fitted to a patient, wherein the fit of the face mask is determined by monitoring the flow rate of gas drawn through the inlet of the face mask upon inhalation by the patient, with the face mask being considered satisfactorily to fit the patient when a substantially regular inhalation waveform is achieved.

2. The apparatus according to claim 1, further comprising a chamber having an outlet in fluid communication with the inlet of the face mask.

3. The apparatus according to claim 2, wherein the chamber includes an inlet through which gas can be introduced.

4. The apparatus according to claim 1, wherein the inlet of the face mask includes a one-way valve for preventing exhalation therethrough.

5. The apparatus according to claim 1, wherein the face mask has an outlet through which gas can be exhaled.

6. The apparatus according to claim 5, wherein the outlet of the face mask includes a one-way valve for preventing inhalation therethrough.

7. The apparatus according to claim 1 wherein the indicator comprises a display for displaying information as to the fit of the face mask to the face of the patient.

8. The apparatus according to claim 7, wherein the display means comprises an LCD display or an LED display.

9. The apparatus according to claim 1, wherein the indicator comprises a second generator for generating a sound when the face mask is fitted satisfactorily to the face of the patient.

10. The apparatus of claim 1 wherein said processor analyzes maximum amplitude over a plurality of breath cycles.

11. A method of ensuring the fit of a face mask to the face of a patient, comprising the steps of:

fitting a face mask having an inlet through which gas can be inhaled to the face of a patient;

monitoring the flow rate of gas drawn through the inlet of the face mask as the patient inhales;

comparing flow rate waveforms to determine if they are substantially uniform over a plurality of breath cycles; and adjusting the position of the face mask as necessary until a substantially regular inhalation waveform is achieved over a plurality of breath cycles.

12. The method according to claim 11, wherein a substantially regular inhalation waveform is achieved when the peak amplitude of the inhalation waveform is substantially at a maximum.

13. The method according to claim 11, further comprising the step of displaying information relating to the fit of the face mask, such as the inhalation waveform and the peak amplitude of the inhalation waveform.

14. The method according to claim 11, further comprising the step of providing an indication as to when the face mask is fitted satisfactorily to the face of a patient.

15. The method according to claim 14, wherein the indication comprises displayed information.

16. The method according to claim 14, wherein the indication comprises a sound.

17. The method of claim 11 wherein said comparing involves comparing maximum amplitude over a plurality of breath cycles.

* * * * *